US006915216B2

(12) United States Patent
Troxler et al.

(10) Patent No.: US 6,915,216 B2
(45) Date of Patent: Jul. 5, 2005

(54) MEASUREMENT DEVICE INCORPORATING A LOCATING DEVICE AND A PORTABLE HANDHELD COMPUTER DEVICE AND ASSOCIATED APPARATUS, SYSTEM AND METHOD

(75) Inventors: Robert Ernest Troxler, Raleigh, NC (US); Andrew Kirk Dummer, Durham, NC (US); James Daniel Pratt, Jr., Raleigh, NC (US); William Finch Troxler, Jr., Raleigh, NC (US); Michael E. Bienvenu, Cary, NC (US); John Pjura, Durham, NC (US); Robyn Lyn Myers, Efland, NC (US); Dirk Steckman, Cary, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 116 days.

(21) Appl. No.: 10/269,843

(22) Filed: Oct. 11, 2002

(65) Prior Publication Data

US 2004/0073382 A1 Apr. 15, 2004

(51) Int. Cl.$^7$ .............................................. G01B 3/00
(52) U.S. Cl. ........................................................ 702/33
(58) Field of Search .......................................... 702/33

(56) References Cited

U.S. PATENT DOCUMENTS

| 5,549,412 | A | * | 8/1996 | Malone ...................... 404/84.1 |
| 5,719,771 | A | | 2/1998 | Buck et al. |
| 5,721,685 | A | | 2/1998 | Holland et al. |
| 5,905,461 | A | | 5/1999 | Neher |
| 5,947,636 | A | | 9/1999 | Mara |
| 5,978,749 | A | | 11/1999 | Likins, Jr. et al. |
| 6,016,713 | A | | 1/2000 | Hale |
| 6,041,582 | A | | 3/2000 | Tiede et al. |
| 6,122,601 | A | * | 9/2000 | Swanson et al. ............ 702/137 |
| 6,301,551 | B1 | | 10/2001 | Piscalko et al. |
| 6,362,778 | B2 | | 3/2002 | Neher |
| 6,388,612 | B1 | | 5/2002 | Neher |
| 6,520,715 | B1 | * | 2/2003 | Smith .......................... 404/75 |
| 6,700,533 | B1 | * | 3/2004 | Werb et al. ............ 342/357.07 |
| 6,718,248 | B2 | * | 4/2004 | Lu et al. ....................... 701/70 |
| 2001/0026240 | A1 | | 10/2001 | Neher |
| 2001/0053970 | A1 | | 12/2001 | Ford et al. |
| 2002/0015354 | A1 | | 2/2002 | Buckelew |
| 2002/0032517 | A1 | | 3/2002 | Buckelew et al. |

FOREIGN PATENT DOCUMENTS

WO          WO 01/73466 A1     10/2001

OTHER PUBLICATIONS

Oloufa, A., "Quality Control of Asphalt Compaction Using GPS–Based System Architecture", *IEEE Robotics & Automation Magazine*, 2002, pp. 29–35.

* cited by examiner

*Primary Examiner*—John Barlow
*Assistant Examiner*—Anthony T. Dougherty
(74) *Attorney, Agent, or Firm*—Alston & Bird LLP

(57) ABSTRACT

A system adapted to determine a property of a paving-related material is provided. Such a system comprises a central computing system housing database, such as a geographic information system (GIS). A measuring device for selectively and directly measuring the property of the paving-related material is remotely disposed with respect to the central computing system and operably engaged with a locating device, such as a global positioning system (GPS) device, for determining a location of the measuring device when the property of the paving-related material is selectively measured thereby. A portable handheld computer device is in communication with the measuring device, the locating device, and the central computing system, wherein the handheld computer device is configured to receive data, comprising the measured property of the paving-related material and the corresponding location of the measuring device when the property is selectively measured thereby, from the measuring device and the locating device, and to communicate the data with the central computing system for incorporation of the data into the database. An associated device, apparatus, and method are also provided.

51 Claims, 1 Drawing Sheet

Figure 1:
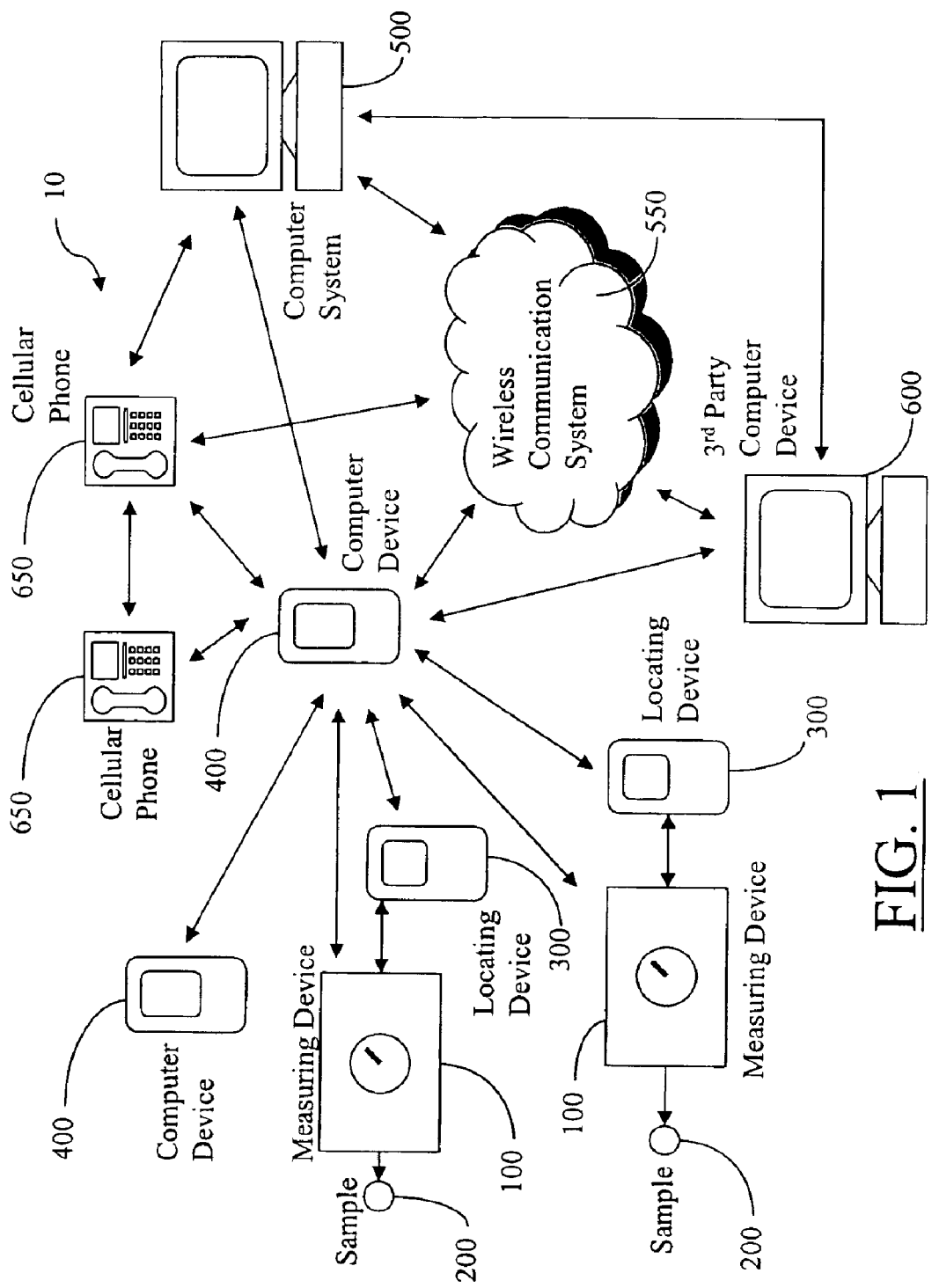

MEASUREMENT DEVICE INCORPORATING A LOCATING DEVICE AND A PORTABLE HANDHELD COMPUTER DEVICE AND ASSOCIATED APPARATUS, SYSTEM AND METHOD

BACKGROUND OF THE INVENTION

1. Field of the Invention

The present invention relates to measurement devices for measuring properties of aggregates, soils, and paving materials and, more particularly, to an apparatus, device, system, and method for determining a property of a paving-related material sample with a measurement device having a locating device operably engaged therewith, the measuring device and the locating device being in communication with a portable computer device which, in turn, may be in communication with a central computer device.

2. Description of Related Art

The process of paving roadways is subject to standards which direct the necessary characteristics of the paving used to form the roadway. As such, actual data from the paving contractor supporting such compliance with the applicable standards is often a mandatory requirement of the entity owning the roadway. Often, the entity is part of the government such as, for example, the Department of Transportation of the state. In order to determine compliance with these various standards, the contractor must often perform certain measurements in the field with certain measuring devices at certain points as the roadway is being paved. However, such measuring devices used in the field often use bulky and cumbersome keypads and/or older technology displays having limited capabilities with respect to collecting, storing, manipulating, and displaying the necessary data. In some instances, the measuring device may require the contractor to manually gather the necessary data and/or keep any notes using paper and a writing utensil. The contractor not only must gather the data from the site, but must also transcribe or otherwise manipulate the collected data such that the data can be presented to the owning entity in a usable and/or the required format.

The described data collection process, though, is prone to inaccuracies, both in the collection of the data and the transcription and/or manipulation of the data. Such a process may also, in some instances, become more complicated if there is uncertainty between the contractor and the owning entity regarding a measurement and/or the location of that measurement. Accordingly, this may lead to disputes since the owning entity is often not present to actually witness the applicable measurements that are generally manually performed by the contractor. Further, the owning entity usually receives a manually prepared record of the time, date, location, and value of each measurement as evidence of the contractor's compliance with the applicable standards.

Thus, there exists a need for a system capable of determining a desired property of a sample of a paving-related material, wherein such a system is further capable of associating other measurements or data, such as location, with the determined property of the sample, so as to provide data having the content and format required by the owning entity, while also providing the owning entity with some assurances of accuracy and reliability of the data.

BRIEF SUMMARY OF THE INVENTION

The above and other needs are met by the present invention which, in one embodiment, provides a system adapted to determine a property of a paving-related material. Such a system comprises a central computing system housing a database, such as a geographic information system (GIS). A measuring device for selectively and directly measuring the property of the paving-related material is remotely disposed with respect to the central computing system and operably engaged with a locating device, such as a global positioning system (GPS) device, for determining a location of the measuring device when the property of the paving-related material is selectively measured thereby. A portable handheld computer device is in communication with the measuring device, the locating device, and the central computing system, wherein the handheld computer device is configured to receive data, comprising the measured property of the paving-related material and the corresponding location of the measuring device when the property is selectively measured thereby, from the measuring device and the locating device, and to communicate the data with the central computing system for incorporation of the data into the database.

Another advantageous aspect of the present invention comprises a device adapted to determine a property of a paving-related material, wherein the device is remotely disposed with respect to a central computing system housing a database, such as a geographic information system (GIS). Such a device includes a measuring device for selectively and directly measuring the property of the paving-related material, the measuring device having a locating device, such as a global positioning system (GPS) device, operably engaged therewith for determining a location of the measuring device when the property of the paving-related material is selectively measured thereby. A portable handheld computer device is in communication with the measuring device and the locating device, and is configured to receive data therefrom. The data comprises the measured property of the paving-related material and the corresponding location of the measuring device when the property is selectively measured thereby. The handheld computer device is further adapted to communicate the data with the central computing system for incorporation of the data into the database.

Yet another advantageous aspect of the present invention comprises an apparatus adapted to determine a property of a paving-related material, wherein the apparatus is remotely disposed with respect to a central computing system housing a database, such as a geographic information system (GIS). Such an apparatus includes a measuring device for selectively and directly measuring the property of the paving-related material, the measuring device having a locating device, such as a global positioning system (GPS) device, operably engaged therewith for determining a location of the measuring device when the property of the paving-related material is selectively measured thereby. The locating device is configured to cooperate with the measuring device to produce data comprising the measured property of the paving-related material and the corresponding location of the measuring device when the property is selectively measured thereby. The locating device and the measuring device are further adapted to communicate the data with the central computing system for incorporation of the data into the database.

Still another advantageous aspect of the present invention comprises a method of determining a property of a paving-related material. First, the property of the paving-related material is selectively and directly measured with a measuring device remotely disposed with respect to a central computing system housing a database, such as a geographic information system (GIS). A location of the measuring device when the property of the paving-related material is selectively measured thereby is concurrently determined with a locating device, such as a global positioning system (GPS) device, operably engaged with the measuring device. Data from the measuring device and the locating device is then directed to a portable handheld computer device, wherein the data comprises the measured property of the paving-related material and the corresponding location of the measuring device when the property is selectively measured thereby. Thereafter, the data is directed from the handheld computer device to the central computing system for incorporation of the data into the database.

Thus, embodiments of the present invention meet the above-identified needs and provide distinct advantages as further detailed herein.

BRIEF DESCRIPTION OF THE SEVERAL VIEWS OF THE DRAWING(S)

Having thus described the invention in general terms, reference will now be made to the accompanying drawing, which is not necessarily drawn to scale, and wherein:

FIG. 1 is a schematic illustration of a system for determining a property of a paving-related material sample with a measurement device having a locating device operably engaged therewith, the measuring device and the locating device being in communication with a portable computer device, according to one embodiment of the present invention.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

FIG. 1 illustrates a system for determining a property of a paving-related material according to one embodiment of the present invention, the system being indicated generally by the numeral 10. Such a system 10 comprises at least one measuring device 100 for measuring a property of a sample 200 of a paving-related material such as, for example, an asphalt paving mix, a soil, or an aggregate. For example, one measuring device 100 may comprise a nuclear density gauge such as, for instance, a Model 3451 Nuclear Density Gauge manufactured by Troxler Electronic Laboratories, for determining the density of the sample 200, while another measuring device 100 may comprise, for instance, a moisture meter such as, for example, a Model 4300 Moisture Meter manufactured by Troxler Electronic Laboratories, for determining the moisture content of the sample 200. Other possibly suitable measuring devices 100 include, for example, any other instrumentation capable of determining density such as a Seismic Pavement Analyzer (SPA), a portable SPA (PSPA) manufactured by Geomedia, a Model H-4140 stiffness gauge distributed by Humboldt Manufacturing, a Model 8000 Falling Weight Deflectometer (FWD) manufactured by Dynatest, and/or various electromagnetic and/or microwave devices such as a ground penetrating radar (GPR) type asphalt instrument from Geophysical Survey Systems or Infrasense, or various RF devices such as the PaveTracker and the PQI from Trans-Tech. Such measuring devices 100 are, in some instances, generally directed to measuring density-related parameters such as, for example, a modulus of elasticity (shear and Young's), a stiffness of the soil or asphalt sample, a void content, and bulk density, wherein the determination of such density-related parameters will be readily appreciated by one skilled in the art. Further, as will be appreciated by one skilled in the art, the measuring device 100 may comprise any other appropriate field or laboratory device, or combinations thereof, capable of performing the desired property measurements of such paving-related materials.

In particularly advantageous embodiments, each measuring device 100 further includes a locating device 300 operably engaged therewith, wherein such a locating device 300 may comprise, for example, a Global Positioning System (GPS) device or other satellite and/or land-based beacon type of locating device implementing, in some instances, a location enhancement scheme such as Differential GPS (DGPS) or a Wide Area Augmentation Scheme (WAAS). However, many different forms of locating devices and/or location enhancement schemes will be appreciated by one skilled in the art as being within the spirit and scope of the present invention. The locating device 300 is configured to determine the position/location of the respective measuring device 100, wherein, in one embodiment, the locating device 300 is configured to determine the position/location in latitude, longitude, and/or altitude coordinates, though any other suitable coordinate system may be used. Since the locating device 300 is operably engaged with the measuring device 100, in addition to the purposes as described herein, the locating device 300 may also be useful in, for example, locating and recovering lost or stolen measuring devices 100 as will be appreciated by one skilled in the art. For example, a measuring device 100/locating device 300 unit may be configured to be in communication with a beacon device (not shown), wherein the beacon device may be further configured to transmit a signal to the measuring device 100/locating device 300 unit if it is determined that the unit is lost, misplaced, or stolen. The unit, in response to the signal, may then be configured to send a signal back to the beacon device indicative of the physical position and/or movement parameters of the unit, as determined by the locating device 300. In other instances, the unit may be configured to send a signal to the beacon device indicative of the physical position and/or movement parameters of the unit if the unit becomes separated from the beacon device by more than a selected distance.

The system 10 further includes a portable handheld computer device 400 such as, for example, a Personal Digital Assistant (PDA) or the like configured to be in wireless communication with each measuring device 100 and/or the respective locating devices 300 though, in some instances, the communication therebetween may be through a wireline system. For example, the handheld computer device 400 may be configured to communicate with the measuring device 100 and/or the locating device 300, or other handheld computer devices 400 using, for example, Bluetooth™ wireless technology, though many other analog and/or digital wireless communication systems and/or modulation schemes may be implemented such as, for example, IR, FSK, PSK, or radio frequency systems, as will be appreciated by one skilled in the art. According to further embodiments of the present invention, a single handheld computer device 400 may be configured to communicate with only a single measuring device 100/locating device 300 unit, with multiple measuring device 100/locating device 300 units, and/or with other handheld computer devices 400 configured for a separate set of measuring device 100/locating device 300 units. In such instances, the handheld computer device 400 and/or the measuring device 100/locating device 300 units can be configured with appropriate electronic coded keys, such as an RF ID tag, or other identifiers so as to ensure that a handheld computer device 400 communicates only with the appropriate measuring device 100/locating device 300 units (and/or other handheld computer devices 400), as will also be appreciated by one skilled in the art. For example, an identifier may comprise a digital key for coding a particular measuring device 100/locating device 300 unit with a handheld computer device 400. Such identifiers may serve other purposes such as, for example, maintaining an inventory of measuring device 100/locating device 300 units or tracking such units in the field.

According to other advantageous aspects of the present invention, the handheld computer device 400 is configured to collect data from the measuring device 100/locating device 300 unit(s), sometimes in real time, wherein such data includes the measured sample property and the location of the measuring device 100 when the sample property is measured thereby. However, the handheld computer device 400 may also be configured to be capable of performing many other tasks in addition to merely collecting the data from the measuring device 100/locating device 300 unit(s). For example, the handheld computer device 400 may be configured to associate, for instance, a time and date stamp, or an electronic identifier for the measuring device 100 (type and/or serial number), the operator thereof, the sample 200, the locating device 300, the handheld computer device 400 receiving the data, the operator thereof, and/or the contractor, with each sample property/measuring device location measurement performed by a measuring device 100/locating device 300 unit and transmitted to the handheld computer device 400. In other instances, the handheld computer device 400 may perform any or all necessary calculations and/or manipulate the data for display to a user, wherein, for example, the raw data could be displayed or the data may be manipulated to produce a variety of graphs and graphics that could then be presented to the user on a screen of the handheld computer device 400. One skilled in the art will appreciate, however, that a wide variety of other functionality may also be implemented in the handheld computer device 400. For example, the handheld computer device 400 may also be configured to have digital filtering or other digital signal processing incorporated therewith, or may be configured with many different capabilities for further enhancing the system 10.

According to further advantageous aspects of the present invention, each handheld computer device 400 is configured to communicate the collected data with a central computer system 500, wherein the central computer system 500 may comprise, for example, a host system associated with the contractor. The central computer system 500 is further configured, in some embodiments, to house a database such as, for example, a geographic information system (GIS). One advantage of such a configuration is that the data may be collected at a central repository having a more expansive, secure, reliable, and stable data storage configuration than the handheld computer device 400 which may have limited memory and which is subject to a relatively hostile environment in the field. The data may be collected from the handheld computer device 400, for example, in real time (as each data element is collected), at the conclusion of a planned series of measurements, at the end of a day, at the end of a job, or on an otherwise periodic basis. The central computer system 500 may also have greater computing and analysis capabilities, as well as more extensive data presentation capabilities, for manipulating the collected data, wherein data from many different handheld computer devices 400 may be collected for comprehensive analysis.

Each handheld computer device 400 may communicate with the central computer system 500 by wireline or by many different wireless systems 550, as will be appreciated by one skilled in the art. For example, the communication may be accomplished via a wide area network (WAN), a local area network (LAN), a satellite network, or otherwise over the Internet. Voice/data network protocols and frequencies that may be supported include, but are not limited to, for example, the global system for mobile communications (GSM)/general packet radio service (GPRS), dual-mode advanced mobile phone service (AMPS)/circuit switched data and code division multiple access (CDMA/1XRTT) (used, for example, in U.S. PCS cellular telephone systems), TDMA, DataTAC, and Mobitex. Other network protocols and frequencies are known in the art and can be supported as well. For example, emerging technologies such as 3G or the IEEE 802.11 protocol may be implemented or direct communication through Bluetooth™ technology may also be used. Further, even a conventional telephone system (POTS) may be implemented. As such, the data may be communicated in many different formats consistent with the many different communications options available, wherein the data may be, for example, included in a simple e-mail message, posted on a web page, or supplied in a complex encrypted data stream.

In one embodiment, the GPRS or CDMA wireless wide area network interface allows communication between the handheld computer device 400 and public digital cellular telephone networks. As such, the handheld computer device 400 may be, in some instances, configured as or may include a cellular telephone capable of allowing the user to communicate with other cellular telephones 650 over the public digital cellular telephone networks. Further, with such various communication options available, software updates and/or relevant data for the handheld computer device 400, the measuring device 100, and/or the locating device 300 may be readily provided thereto by the central computer system 500 or any other authorized computer system associated with, for instance, the manufacturer of the particular component. In the alternative, such software and/or data may also accessed by the handheld computer device 400 at a specific site and then distributed to the measuring device 100 and/or locating device 300, if necessary.

According to further advantageous aspects of the present invention, the handheld computer device 400 may be configured to communicate the collected data with a third party computer device 600 in addition to, or instead of, with the central computer system 500 associated with the contractor. For example, the third party computer device 600 may be associated with the owning entity and/or the particular state Department of Transportation. In such instances, the data collected from the measuring device 100/locating device 300 unit(s) by the handheld computer device 400 may be associated with, for example, a time and date stamp, or an electronic identifier for the measuring device 100 (type and/or serial number), the operator thereof, the sample 200, the locating device 300, the handheld computer device 400 receiving the data, the operator thereof, and/or the contractor, with each sample property/measuring device location measurement performed by the measuring device 100/locating device 300 unit and transmitted to the handheld computer device 400. The data may be collected from the handheld computer device 400, for example, in real time (as each data element is collected), at the conclusion of a planned series of measurements, at the end of a day, at the end of a job, or on an otherwise periodic basis, and then communicated with the third party computer device 600, preferably without allowing the raw data to be altered or otherwise manipulated by the operator of the measuring device 100, the locating device 300, or the handheld computer device 400, or by the contractor. For example, the data could be written into a read-only file or the third party could assign a software security key to the data file on the handheld computer device 400 so as to deter any tampering with the data written to the file. However, in some instances, the handheld computer device 400 may be configured to provide a graphic depiction, such as a variety of graphs or graphics, of the data for display to the third party, wherein the graphical depiction would be provided in addition to the untouched raw data.

A system 10 as described herein provides distinct advantages over an integrated measuring device capable of addressing such data-related issues as previously described. For example, the manufacturer does not have to stock parts or pay for extra labor in the construction process as would be necessary for an integrated measuring device. Further, measuring device-specific software, I/O systems, and processors are not necessary. The manufacturer further saves costs by not having to develop specific hardware and/or software for the particular measuring device. In addition, older technology measuring devices 100 may be significantly and readily updated by configuring the handheld computer device 400 to function as the user interface therefor, while a variety of programming languages and protocols may allow greater functionality and flexibility in the capabilities of the measuring devices 100 than previously possible. Also, the measuring device 100 and/or the locating device 300 may be readily configured or updated via a communication from the handheld computer device 400 and/or the central computer system 500 where, for example, the measuring device 100 and/or the locating device 300 may be remotely calibrated or have calibration parameters directed thereto. In other instances, for example, the measuring device 100 and/or the locating device 300 may be provided with a digital key from the central computing device 500 to allow the measuring device 100 and/or the locating device 300 to be manually manipulated or manipulated via the handheld computing device 400.

The customer (contractor) would also realize benefits from a system 10 as described. For example, the locating device 300 and the handheld computer device 400 are, in some instances, commercially available devices which may be readily configured for the functions as described herein. Accordingly, initial purchase costs and repair costs for the customer would be lower than specialty devices and the commercially available devices could be used for other purposes alternatively or in addition to the purposes as described herein. The customer could also readily alter existing software applications or independently develop software applications to custom tailor the system 10 to suit particular needs.

Many modifications and other embodiments of the invention set forth herein will come to mind to one skilled in the art to which this invention pertains having the benefit of the teachings presented in the foregoing descriptions and the associated drawings. For example, one skilled in the art will readily appreciate that a device comprising a measuring device, a locating device, and a portable handheld computer device may be provided, as well as an apparatus comprising a measuring device and an associated locating device. More particularly, for instance, the measuring device and locating device may be configured to cooperate to send the relevant data directly to a central computer system or, in other instances, the measuring device may be configured to store the relevant data, which may then later be downloaded to a computer device for analysis. Further, one skilled in the art will also appreciate that the systems, devices, and methods described herein will readily lend themselves to one or more corresponding methods, computer devices, computer software program products, and/or the like within the spirit and scope of the present invention. In addition, the concepts, systems, apparatuses, and methods presented herein may be applicable in many different fields, besides the paving industry, in which it would be advantageous to combine the position indication of a GPS device with a particular measurement or event. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system adapted to determine a property of a paving-related material, said system comprising:
   a computing system housing a database;
   a measuring device for selectively and directly measuring and determining the property of the paving-related material, the measuring device being remotely disposed with respect to the computing system;
   a locating device operably engaged with the measuring device for determining a location of the measuring device when the property of the paving-related material is selectively and directly measured and determined thereby; and
   a computer device in communication with the measuring device, the locating device, and capable of communicating with the computing system, the handheld computer device being configured to receive data from the measuring device and the locating device, the data comprising the measured property of the paving-related material and the corresponding location of the measuring device when the property is selectively and directly measured and determined thereby, and to selectively communicate the data with the computing system for incorporation of the data into the database.

2. A system according to claim 1 wherein the measuring device is further adapted to directly measure at least one of a density, a density-related parameter; and a moisture content of at least one of a soil, an aggregate, and an asphalt paving mix.

3. A system according to claim 1 wherein the computer device is further adapted to receive input from an operator thereof.

4. A system according to claim 1 wherein the computer device is configured to communicate with the computing system via at least one of a wireless and a wireline network.

5. A system according to claim 1 wherein the computer device is further configured to be capable of accessing the database and receiving data therefrom.

6. A system according to claim 1 wherein the measuring device is selected from the group consisting of a nuclear density gauge, a seismic pavement analyzer, a stiffness gauge, a falling weight deflectometer, a ground penetrating radar device, a radio frequency device, an electromagnetic device, a microwave device, and combinations thereof.

7. A system according to claim 1 wherein the locating device is further configured to be capable of indicating the location of the measuring device, independently or the property measurement, so as to allow the measuring device to be located and tracked.

8. A system according to claim 1 wherein the computer device is further adapted to direct the data from the measuring device and the locating device to a third party device without allowing the data to be modified by an operator of the computer device.

9. A system according to claim 1 wherein the computer device is further configured to associate a time and date stamp with the data when the property is measured by the measuring device.

10. A system according to claim 1 wherein the computer device is further configured to be capable of manipulating the data.

11. A system according to claim 1 wherein the database comprises a geographic information system (GIS).

12. A system according to claim 1 wherein the locating device comprises a global positioning system (GPS) device.

13. A system according to claim 1 wherein at least one of the measuring device and the locating device is configured to receive a communication from at least one of the computing system and the computer device.

14. A device adapted to determine a property of a paving-related material, the device being further adapted to be remotely disposed with respect to a computing system housing a database, said device comprising:
 a measuring device for selectively and directly measuring and determining the property of the paving-related material;
 a locating device operably engaged with the measuring device for determining a location of the measuring device when the property of the paving-related material is selectively and directly measured and determined thereby; and
 a computer device in communication with the measuring device and the locating device, and configured to receive data therefrom, the data comprising the measured property of the paving-related material and the corresponding location of the measuring device when the property is selectively and directly measured and determined thereby, the computer device being adapted to be capable of communicating the data with the computing system for incorporation of the data into the database.

15. A device according to claim 14 wherein the measuring device is further adapted to directly measure at least one of a density, a density-related parameter, and a moisture content of at least one of a soil, an aggregate, and an asphalt paving mix.

16. A device according to claim 14 wherein the computer device is further adapted to receive input from an operator thereof.

17. A device according to claim 14 wherein the computer device is further adapted to communicate with the computing system via at least one of a wireless and a wireline network.

18. A device according to claim 14 wherein the computer device is further adapted to ba capable of accessing the database and receiving data therefrom.

19. A device according to claim 14 wherein the measuring device is selected from the group consisting of a nuclear density gauge, a seismic pavement analyzer, a stiffness gauge, a falling weight deflectometer, a ground penetrating radar device, a radio frequency device, an electromagnetic device, a microwave device, and combinations thereof.

20. A device according to claim 14 wherein the locating device is further configured to be capable of indicating the location of the measuring device, independently of the property measurement, so as to allow the measuring device to be located and tracked.

21. A device according to claim 14 wherein the computer device is further adapted to direct the data from the measuring device and the locating device to a third party device without allowing the data to be modified by an operator of the computer device.

22. A device according to claim 14 wherein the computer device is further configured to associate a time and date stamp with the data when the property is measured by the measuring device.

23. A device according to claim 14 wherein the computer device is further configured to be capable of manipulating the data.

24. A device according to claim 14 wherein the locating device comprises a global positioning system (GPS) device.

25. A device according to claim 14 wherein at least one of the measuring device and the locating device is at least one of configured to receive a communication from the computing system and adapted to receive a communication from the computer device.

26. An apparatus adapted to determine a property of a paving-related material, said apparatus comprising:
 a measuring device for selectively and directly measuring and determining the property of the paving-related material; and
 a locating device operably engaged with the measuring device for determining a location of the measuring device when the property of the paving-related material is selectively and directly measured and determined thereby, the locating device being configured to cooperate with the measuring device to produce data comprising the measured property of the paving-related material and the corresponding location of the measuring device when the property is selectively and directly measured and determined thereby.

27. An apparatus according to claim 26 wherein the measuring device is further adapted to directly measure at least one of a density, a density-related parameter, and a moisture content of at least one of a soil, an aggregate, and an asphalt paving mix.

28. An apparatus according to claim 26 further comprising a computer device capable of communicating with the measuring device and the locating device and configured to receive the data therefrom, the computer device being further adapted to be capable of communicating the data with a computing system remotely disposed with respect to the apparatus, for incorporation of the data into a database housed by the computing system.

29. An apparatus according to claim 28 wherein the computer device is further adapted to receive input from an operator thereof.

30. An apparatus according to claim 28 wherein the computer device is further adapted to communicate with the computing system via at least one of a wireless and a wireline network.

31. An apparatus according to claim 28 wherein the computer device is further adapted to be capable of accessing the database and receiving data therefrom.

32. An apparatus according to claim 28 wherein the computer device is further adapted to direct the data from the measuring device and the locating device to a third party device without allowing the data to be modified by an operator of the computer device.

33. An apparatus according to claim 28 wherein the computer device is further configured to associate a time and date stamp with the data when the property is measured by the measuring device.

34. An apparatus according to claim 28 wherein the computer device is further configured to he capable of manipulating the data.

35. An apparatus according to claim 26 wherein the measuring device is selected from the group consisting of a nuclear density gauge, seismic pavement analyzer, a stiffness gauge, a falling weight deflectometer, a ground penetrating radar device, a radio frequency device, an electromagnetic device, a microwave device, and combinations thereof.

36. An apparatus according to claim 26 wherein the locating device is further configured to be capable of indicating the location of the measuring device, independently of the property measurement, so as to allow the measuring device to be located and tracked.

37. An apparatus according to claim 26 wherein the locating device comprises a global positioning system (GPS) device.

38. An apparatus according to claim 26 wherein at least one of the measuring device and the locating device is adapted to receive a communication from at least one of a computing system and a computer device.

39. A method of determining a property of a paving-related material, said method comprising:

selectively and directly measuring and determining the property of the paving-related material with a measuring device remotely disposed with respect to a computing system housing a database;

concurrently determining a location of the measuring device when the property of the paving-related material is selectively and directly measured and determined thereby with a locating device operably engaged with the measuring device;

selectively directing data from at least one of the measuring device and the locating device to a computer device capable of communicating therewith, the data comprising the measured property of the paving-related material and the corresponding location of the measuring device when the property is selectively and directly measured and determined thereby;

selectively directing the data from the computer device to the computing system; and incorporating the data into the database.

40. A method according to claim 39 wherein directly measuring the property further comprises directly measuring at least one of a density, a density-related parameter, and a moisture content of at least one of a soil, an aggregate, and an asphalt paving mix with the measuring device.

41. A method according to claim 39 further comprising receiving input into the computer device from an operator thereof before directing the data from the computer device to the computing system.

42. A method according to claim 39 wherein directing the data from the computer device to the computing system further comprises directing the data from the computer device to the computing system via at least one of a wireless and a wireline network.

43. A method according to claim 39 further comprising accessing the database with the computer device so as to receive data therefrom at the computer device.

44. A method according to claim 39 wherein directly measuring the property further comprises directly measuring the property of the paving-related material with a nuclear density gauge, a seismic pavement analyzer, a stiffness gauge, a falling weight deflectometer, a ground penetrating radar device, a radio frequency device, an electromagnetic device, a microwave device, or combinations thereof.

45. A method according to claim 39 further comprising determining the location of the measuring device with the locating device, independently of the property measurement by the measuring device, so as to locate and track the measuring device.

46. A method according to claim 39 wherein directing the data from the computer device further comprises directing the data from the computer device to a third party device without allowing the data to be modified by on operator of the computer device.

47. A method according to claim 39 further comprising associating a time and date stamp with the data concurrently with directly measuring the property of the paving-related material.

48. A method according to claim 39 further comprising manipulating the data with the computer device prior to directing the data from the computer device.

49. A method according to claim 39 wherein directly measuring the property of the paving-related material further comprises directly measuring the property of the paving-related material with a measuring device remotely disposed with respect to a computing system housing a geographic information system (GIS).

50. A method according to claim 39 wherein concurrently determining a location of the measuring device further comprises concurrently determining a location of the measuring device when the property of the paving-related material is measured thereby with a global positioning system (GPS) device operably engaged with the measuring device.

51. A method according to claim 39 further comprising directing a communication to at least one of the measuring device and the locating device from at least one of the computing system and the computer device.

* * * * *